US009970871B2

(12) United States Patent
Slurink et al.

(10) Patent No.: US 9,970,871 B2
(45) Date of Patent: May 15, 2018

(54) TESTING APPARATUS AND TESTING METHOD OF VAPORIZERS OF ELECTRONIC CIGARETTES

(71) Applicant: Sluis Cigar Machinery B.V., Kampen (NL)

(72) Inventors: Oscar Slurink, Heino (NL); Lambert Wijnand Breman, Kampen (NL); Abraham Van Den Berg, Ijsselmuiden (NL)

(73) Assignee: SLUIS CIGAR MACHINERY B.V., Kampen (NL)

( * ) Notice: Subject to any disclaimer, the term of this patent is extended or adjusted under 35 U.S.C. 154(b) by 0 days. days.

(21) Appl. No.: 15/510,426

(22) PCT Filed: Sep. 10, 2015

(86) PCT No.: PCT/NL2015/050627
§ 371 (c)(1),
(2) Date: Mar. 10, 2017

(87) PCT Pub. No.: WO2016/039625
PCT Pub. Date: Mar. 17, 2016

(65) Prior Publication Data
US 2017/0241906 A1 Aug. 24, 2017

(30) Foreign Application Priority Data
Sep. 12, 2014 (NL) .................................... 2013463

(51) Int. Cl.
*G01N 21/55* (2014.01)
*G01N 21/59* (2006.01)
*A24F 47/00* (2006.01)

(52) U.S. Cl.
CPC ........... *G01N 21/59* (2013.01); *A24F 47/008* (2013.01); *G01N 21/55* (2013.01)

(58) Field of Classification Search
CPC ......... G01N 21/00; G01N 21/55; G01N 21/59
(Continued)

(56) References Cited

U.S. PATENT DOCUMENTS 3,618,365 A 11/1971 McArthur
4,058,120 A 11/1977 Caparrelli et al.
(Continued)

FOREIGN PATENT DOCUMENTS

CN 101523572 A 9/2009
EP 2944206 A1 11/2015
(Continued)

OTHER PUBLICATIONS

International Search Report and Written Opinion dated Dec. 17, 2015 for Application No. PCT/NL2015/050627.
(Continued)

Primary Examiner — Roy M Punnoose
(74) Attorney, Agent, or Firm — Patterson & Sheridan, L.L.P.

(57) ABSTRACT

A testing apparatus for testing vaporizers of electronic cigarettes, or electronic cigarettes or parts thereof comprising the vaporizers, comprises a movable holding construction part provided with multiple holding units each for holding a vaporizer, or electronic cigarette or part thereof comprising the vaporizer. A channel construction part moves synchronously with the holding construction part and is provided with multiple first channels. An inlet opening of each first channel is in fluid communication with a vapor output of a vaporizer in an associated holding unit. The outlet openings of the first channels move along an outlet opening trajectory. A fluid duct has a stationary inlet port adjacent to the outlet opening trajectory. The fluid duct is
(Continued)

connected to a fluid pump to create a fluid flow in the fluid duct in a direction away from the inlet port. A vapor sensor is arranged in the fluid duct.

20 Claims, 7 Drawing Sheets

(58) Field of Classification Search
USPC .......................................................... 356/437
See application file for complete search history.

(56) References Cited

U.S. PATENT DOCUMENTS

| | | | |
|---|---|---|---|
| 4,227,400 A | 10/1980 | Nienow et al. | |
| 9,645,134 B1* | 5/2017 | Farmen | G01N 33/49 |
| 2010/0044461 A1 | 2/2010 | Nishikawa et al. | |
| 2012/0318882 A1 | 12/2012 | Abehasera | |
| 2014/0202474 A1 | 7/2014 | Peleg et al. | |
| 2014/0300480 A1 | 10/2014 | Xiang | |
| 2017/0020195 A1* | 1/2017 | Cameron | A24F 47/008 |
| 2017/0030882 A1* | 2/2017 | Skoda | G01N 33/15 |
| 2017/0086496 A1* | 3/2017 | Cameron | B25F 1/04 |

FOREIGN PATENT DOCUMENTS

| | | |
|---|---|---|
| NL | 7100754 A | 7/1971 |
| WO | 2014161190 A1 | 10/2014 |

OTHER PUBLICATIONS

Search Report and Written Opinion dated Apr. 1, 2015 for Netherland Application No. NL2013463.

* cited by examiner

TESTING APPARATUS AND TESTING METHOD OF VAPORIZERS OF ELECTRONIC CIGARETTES

FIELD OF THE INVENTION

The invention relates to the field of testing of electronic cigarettes, and more specifically to testing of vaporizers of electronic cigarettes.

BACKGROUND OF THE INVENTION

A vaporizer of an electronic cigarette comprises a liquid holder forming a chamber with a filler material retaining a liquid to be vaporized, a heating element, input terminals connected to the heating element for electrically powering the heating element, and a vapour output, whereby the vaporizer is to generate vapour emerging from the vapour output when a current flows through the input terminals in the heating element. In operation, in the electronic cigarette an air flow is detected, generated by a user drawing in air through the electronic cigarette. The detection of the flow triggers a supply of electrical power from a battery to the input terminals of the heating element, which as a consequence heats up and causes part of the liquid in the vaporizer to vaporize. The vapour emerging from the vapour output of the vaporizer then mixes with the air drawn in by the user.

Since this effect is crucial in the functioning of an electronic cigarette, in the manufacture of the electronic cigarette quality needs to be assured in that a proper functioning of the vaporizer is to be verified in a test. This test can be performed on a vaporizer as such, or on a vaporizer as part of an assembly including the vaporizer, such as a complete electronic cigarette. If the test shows that the vaporizer malfunctions, then the vaporizer, or the assembly including the vaporizer, is to be rejected and removed from a production line for discarding or analysis of the defect.

With the required high production rate in electronic cigarette manufacturing industry, the test should be performed mechanically and automatically, without human intervention, in particular manual intervention.

Thus, a need exists to provide an apparatus and method to satisfy such requirement.

SUMMARY OF THE INVENTION

It would be desirable to provide an improved, or at least alternative apparatus and method for testing vaporizers of electronic cigarettes. It would also be desirable to provide such apparatus and method allowing a continuous testing of vaporizers of electronic cigarettes. It would further be desirable to provide such apparatus having a simple construction requiring a low number of parts. It would also be desirable to provide such apparatus and method which produce a reliable result.

To better address one or more of these concerns, in a first aspect of the invention a testing apparatus is provided for testing vaporizers of electronic cigarettes, or electronic cigarettes or parts thereof comprising the vaporizers, each vaporizer comprising a liquid holder forming a chamber with a filler material retaining a liquid to be vaporized, a heating element, input terminals connected to the heating element for electrically powering the heating element, and a vapour output, whereby the vaporizer is to generate vapour emerging from the vapour output when a current flows through the input terminals in the heating element. The testing apparatus comprises:

a holding construction part provided with multiple holding units each for holding a vaporizer, or a cigarette or part thereof comprising the vaporizer, wherein the holding units are positioned at a holding distance from each other, and wherein the holding construction part is movable whereby the holding units are moved along a holding unit trajectory;

a channel construction part provided with multiple first channels each having an inlet opening and an outlet opening, wherein each first channel is associated with a respective holding unit, wherein the inlet opening of each first channel is located to be in fluid communication with the vapour output of a vaporizer in the associated holding unit, and wherein the channel construction part is adapted to be moved in synchronism with the holding construction part whereby the outlet openings of the first channels move along an outlet opening trajectory;

a fluid duct having an inlet port located to be adjacent to the outlet opening trajectory, wherein the fluid duct is connected to a fluid pump to create a fluid flow in the fluid duct in a direction away from the inlet port, and wherein the channel construction part moves relative to the inlet port of the fluid duct; and a vapour sensor arranged in the fluid duct.

With the testing apparatus, vaporizers as such can be tested, in particular on their ability to produce at least a required amount of vapour when the vaporizer is electrically powered. Furthermore, a vaporizer being part of an assembly of a vaporizer and another part of an electronic cigarette can be tested. Also, a vaporizer being part of an essentially complete electronic cigarette can be tested with the testing apparatus.

In the testing apparatus, the vaporizers, or cigarettes or parts thereof comprising a vaporizer (hereinafter briefly: the vaporizers), are mechanically transported in a holding construction part which has multiple holding units which each are configured to hold one vaporizer in a predetermined position and orientation, to provide a high degree of predictability of a spatial position and orientation in time for each vaporizer. This facilitates a mechanical and automatic performance of a test, which requires contacting the vaporizer with external structures.

A holding unit can be configured in different forms. As an example, a holding unit may comprise a resilient material having a recess for accommodating a vaporizer by friction through a clamping force exerted by the resilient material as it is deformed by the vaporizer. Alternatively, the holding unit may be made from a rigid material having a recess for accommodating a vaporizer by friction through a clamping force exerted on the vaporizer as the latter is deformed. As another example, a holding unit may comprise a gripper having gripper parts engaging a vaporizer.

The holding construction part comprises the holding units which are moved or conveyed along a holding unit trajectory. The holding construction part can have different configurations. A configuration of the holding construction part may depend on the holding unit trajectory. As an example, when the holding unit trajectory is a straight trajectory, the holding construction part may comprises a belt or the like provided with holding units. The belt may be running around two or more rollers such that between two rollers the belt follows a straight trajectory. As another example, when the holding unit trajectory is a curved trajectory, the holding construction part may comprise a belt or the like provided with holding units, the belt running around two or more rollers. Between two rollers, the belt may be guided along a curved guide such that between the two rollers the belt follows a curved trajectory. As a further preferred example, the holding unit trajectory may be circular, wherein the holding construction part may comprise a rotating body, such as a circular ring or plate, carrying the holding units and moving them in rotation along the holding unit trajectory.

In an embodiment of the testing apparatus according to the invention, the testing apparatus further comprises: a supply unit which places the vaporizers, or cigarettes or parts thereof comprising the vaporizers, in the holding units of the holding construction part at a receiving location along the holding unit trajectory so that the vaporizers, or cigarettes or parts thereof comprising the vaporizers, are transported along at least part of the holding unit trajectory; and a discharge unit which removes the vaporizers, or cigarettes or parts thereof comprising the vaporizers, from the holding units at a discharge location along the holding unit trajectory.

In the testing apparatus, the channel construction part establishes a fluid communication between the vapour output of one vaporizer at the time on the one hand, and the fluid duct on the other hand. The channel construction part comprised multiple first channels, each one associated with a different holding unit. Each first channel comprises an inlet opening which is located to be adjacent to a vapour output of a vaporizer held in the associated holding unit. Such location will be maintained while the channel construction part moves, since the channel construction part is adapted to be moved in synchronism with the holding construction part. With a movement of the channel construction part, the outlet openings of the first channels move along an outlet opening trajectory. The inlet port of the fluid duct is located to be adjacent to the outlet opening trajectory, such that vapour generated by a vaporizer may pass through the first channel when the first channel is in fluid communication with the fluid duct. The latter fluid communication is only established when the outlet opening of the first channel overlaps with the inlet port of the fluid duct, which relative position and timing thereof is determined by the nature of the movement of the channel construction part relative to the inlet port of the fluid duct.

The fluid duct is connected to a fluid pump, in particular a fluid pump creating a low(ered) pressure in the fluid duct, so that vapour generated in the vaporizer is sucked through the associated first channel into the fluid duct, when the outlet opening of the first channel overlaps with the inlet port of the fluid duct. The vapour in the fluid flow is mixed with an environmental gas, e.g. air, being present in the environment of the testing apparatus, and flowing along and/or through the vaporizer while testing it.

In case the vaporizer is part of a complete operable electronic cigarette, the low(ered) pressure in the fluid duct will initially generate a flow of air in the electronic cigarette (where the vapour output will be in fluid communication with the mouthpiece of the electronic cigarette), which will trigger an electrical power supply to the heating element of the vaporizer from a battery, which in turn will trigger the generation of vapour in the vaporizer. The vapour will be drawn into the flow of air, and will flow into and through the fluid duct.

Using an appropriate vapour sensor in the fluid duct, the vapour may be detected to confirm that the vaporizer functions properly. From the detection of the vapour, a test result of the vaporizer concerned may be determined, i.e. an approval or a rejection of the vaporizer. An malfunction of a vaporizer may e.g. be caused by a broken heating element, a broken connection between an input terminal of the heating element and a remainder thereof, a low amount of liquid to be vaporized, or an absence of liquid to be vaporized.

In case of testing a vaporizer as such, not being part of a complete operable electronic cigarette, electrical power needs to be supplied to the input terminals of the vaporizer when the outlet opening of the first channel overlaps with the inlet port of the fluid duct to test whether the vaporizer produces vapour under such conditions. For this purpose, the input terminals of the vaporizer need to be brought into contact with a power supply providing electrical power to the heating element of the vaporizer at least when the outlet opening of the first channel overlaps with the inlet port of the fluid duct. An embodiment of such power supply is provided below.

A movement of the holding construction part and the channel construction part may be at a constant speed or at a variable speed. The variable speed may vary between zero speed and maximum speed. The movement may be intermittent. The speed may be adjustable, e.g. dependent from the product to be tested: a vaporizer, or a cigarette or part thereof comprising the vaporizer, and/or dependent from the position of the product relative to the inlet port of the fluid duct, e.g. having a lower speed when the outlet opening of the associated first channel overlaps with the inlet port of the fluid duct, and a higher speed when no outlet opening of any first channel overlaps with the fluid duct, before a next outlet opening of a next first channel associated with a next vaporizer to be tested overlaps with the inlet port of the fluid duct.

In an embodiment of the testing apparatus according to the invention, the inlet port of the fluid duct is stationary, i.e. stationary relative to the movable holding construction part and channel construction part. The fluid duct may also be stationary relative to the movable holding construction part and channel construction part. A stationary inlet port and/or fluid duct may have a simple structure requiring low or no maintenance or replacement of worn parts.

In an embodiment of the testing apparatus according to the invention, the channel construction part further comprises a plurality of second channels each having an inlet opening and an outlet opening, wherein the inlet openings of the second channels are open to the environment, and wherein each outlet opening of a second channel is located in the channel construction part between two consecutive outlet openings of the first channels to be on the outlet opening trajectory.

In such structure, alternatingly an outlet opening of a first channel and an outlet opening of a second channel will overlap with the inlet port of the fluid duct. When the outlet opening of the first channel overlaps with the inlet port, vapour produced by the vaporizer associated with the first channel is drawn into the fluid duct, if the vaporizer functions properly, to be detected by the vapour sensor associated with the fluid duct. Next, when the outlet opening of the second channel overlaps with the inlet port, environmental gas, e.g. air, is drawn into the fluid duct. The environmental gas flushes the fluid duct and removes vapour previously drawn into the fluid duct, at least at the location of the sensing region of the vapour sensor. Next, when the outlet opening of a further first channel overlaps with the inlet port, it is ensured that only any vapour produced by the further vaporizer associated with the further first channel will be present in the fluid duct, and no vapour produced earlier by other vaporizers is present in the fluid duct, at least at the location of the sensing region of the vapour sensor.

In an embodiment of the testing apparatus according to the invention, the inlet port of the fluid duct extends along a portion of said outlet opening trajectory to be in fluid communication with a first channel, a combination of a first channel and a second channel, or a second channel, upon movement of the channel construction part.

In such structure, there always is a fluid flow in the fluid duct, either from the first channel, or from the combination of the first channel and the second channel, or from the second channel. This promotes a stabilization of the flow characteristics, in particular lowering or minimizing or preventing turbulence in the fluid duct. This allows the operation of the vapour sensor to be more accurate, since transitions in the fluid flow composition (vapour and environmental gas alternating with environmental gas only) will be more distinct.

In an embodiment of the testing apparatus according to the invention, the inlet opening of each first channel is provided with a resilient sealing element configured to contact the vapour output of a vaporizer in the associated holding unit.

In the operation of the testing apparatus, it is beneficial when as much vapour as possible produced by a vaporizer, with respect to environmental gas, is drawn into the fluid duct. Sealing the contact area between the vapour output and the inlet opening of the associated first channel prevents additional environmental gas to enter the inlet opening of the first channel to mix with the vapour from the vaporizer, thereby diluting the vapour and disturbing the fluid flow from the vaporizer to the fluid duct. Thus, a vapour content of the fluid flow can be optimized, to thereby provide an optimum performance of the vapour sensor.

In an embodiment of the testing apparatus according to the invention, the vapour sensor is configured to provide a sensing signal indicating an amount of vapour present in the fluid duct, wherein the testing apparatus further comprises a control device configured to:
  acquire the sensing signal after the inlet port of the fluid duct has come in fluid communication with a first channel;
  comparing the sensed amount of vapour with a predetermined lower and/or higher threshold; and
  provide a control signal indicating a rejection of the vaporizer when the sensed amount of vapour is below the predetermined lower threshold or above the predetermined higher threshold, or indicating an approval of the vaporizer otherwise.

In the testing of vaporizers by the testing apparatus, some of the vaporizers may not produce vapour, or may produce an insufficient amount of vapour for the intended use of the electronic cigarette of which the vaporizer is to form part. The vapour sensor senses the amount of vapour, if any, produced by the vaporizer. The control device may be integrated with the vapour sensor, or may be separate therefrom. The control device comprises a processor to compare the sensed amount to at least one predetermined threshold, i.e. an expected amount of vapour within a specification of the vaporizer. The threshold may be a lower threshold which should be exceeded by the amount of vapour produced by the vaporizer. The threshold may also be a higher threshold which should not be exceeded by the amount of vapour produced by the vaporizer. In case of a lower threshold not being exceeded, and in case of a higher threshold being exceeded, the vaporizer is rejected. Otherwise, i.e. when the lower threshold is exceeded, and/or when the higher threshold is not exceeded, the vaporizer is approved. The control device provides a control signal indicating the rejection or approval of the vaporizer.

In an embodiment of the testing apparatus according to the present invention, the control device further is configured to actuate an ejection device if the sensing signal indicates the amount of vapour to be below the predetermined lower threshold or above the predetermined higher threshold. The ejection device is actuated to remove the vaporizer concerned from the production process for lacking the required quality. The ejection device may be included in a discharge unit of the testing apparatus, or may be arranged further downstream in a discharge path of the vaporizers.

In an embodiment of the testing apparatus according to the invention, the vapour sensor comprises a light detector, wherein the light detector is adapted to sense a transmission or reflection of light from a light source to a path of vapour in the fluid duct.

The vapour produced by a vaporizer comprises fine particles which block light transmission, and which reflect light. Thus, when an amount of vapour per unit of volume increases, a light transmission through the vapour decreases, and a light reflection by the vapour increases. Conversely, when an amount of vapour per unit of volume decreases, a light transmission through the vapour increases, and a light reflection by the vapour decreases. These properties of the vapour can be utilized by the light detector acting as a vapour sensor.

A light source, e.g. emitting visible or invisible (ultraviolet or infrared) light, may be arranged, e.g. in the fluid duct or in a wall thereof, to emit light radiation towards a path of the vapour in the fluid duct. A light detector may be arranged at a side of the path of the vapour in the fluid duct to essentially detect light transmitted through the vapour and/or a light detector may be arranged at another side of the path of the vapour in the fluid duct to essentially detect light reflected by the vapour.

In an embodiment of the testing apparatus according to the invention, the testing apparatus further comprises a contact construction part provided with multiple contact members, wherein each contact member is associated with a respective holding unit, and is configured to contact at least one input terminal of the vaporizer in the associated holding unit, and wherein the contact construction part is adapted to be moved in synchronism with the holding construction part.

In the testing of vaporizers, or electronic cigarettes or parts thereof comprising the vaporizer, it is important that the vapour output of the vaporizer is contact with the inlet opening of the associated first channel. The contact member may be operated to displace the vaporizer, or electronic cigarette or part thereof comprising the vaporizer, such that the vaporizer has the desired contact with the inlet opening of the associated first channel. In particular, the contact member may displace the vaporizer, or electronic cigarette or part thereof comprising the vaporizer, to bring the inlet opening of the first channel in fluid communication with the vapour output of a vaporizer using the resilient sealing element, and deforming it to provide a reliable sealing.

When vaporizers are tested that do not form part of a complete operable electronic cigarette, the input terminals of the heating element of the vaporizer need to be electrically powered to have the vaporizer produce vapour at least when the associated first channel overlaps with the inlet port of the fluid duct. For this purpose, the testing apparatus may comprise the contact construction part having at least one electrical contact member to contact at least one input terminal of the vaporizer held in an associated holding unit.

The contact member may have one or more electrical contacts to contact respective one or more input terminals of the heating element of the vaporizer. Beside this electrical function, the contact member also may have the mechanical function as described in the preceding paragraph.

A vaporizer may have an enclosure being one of the input terminals of the heating element, and having an electrical mass connection with the testing apparatus when the vaporizer is held in the associated holding unit. Then, another input terminal may be contacted by a contact of the contact member to electrically power the heating element when a voltage is applied to the contact member.

In an embodiment of the testing apparatus according to the invention, wherein the contact members are electrical contact members, and wherein the electrical contact members are configured to contact at least one input terminal of the vaporizer in the associated holding unit, the testing apparatus further comprises:

a supply construction part provided with:

multiple electrical slip contacts, wherein each slip contact is associated with a respective contact member, wherein the slip contact is electrically connected to an associated contact member, and wherein the supply construction part is adapted to be moved in synchronism with the contact construction part; and at least one power supply terminal configured to electrically contact and power a slip contact associated with a contact member, which in turn is associated with a holding unit, when an outlet opening of a first channel associated with said holding unit is in fluid communication with the inlet port of the fluid duct, wherein the slip contacts are adapted to move relative to the power supply terminal.

The use of slip contacts allows to provide electrical power from the power supply terminal to a contact member, and thereby to a heating element of a vaporizer held in a holding unit associated with the contact member, at an accurately mechanically predetermined time period to cause the vaporizer to produce vapour when an outlet opening of a first channel associated with said holding unit is in fluid communication with the inlet port of the fluid duct (in other words: when an outlet opening of the first channel associated with said holding unit overlaps with the inlet port of the fluid duct). Although it is feasible to have the vaporizer also produce vapour in the testing apparatus, and although it may be practical to start the vapour production of the vaporizer already a brief period before an actual overlap between the outlet opening of the first channel and the input port of the fluid duct takes place, a vapour production during other periods of residence time in the testing apparatus will normally serve no purpose and wastes fluid to be vaporized.

In an embodiment of the testing apparatus according to the invention, the power supply terminal is stationary, i.e. stationary relative to the movable holding construction part, channel construction part, and contact construction part. A stationary power supply terminal may have a simple structure requiring little maintenance and replacement of worn parts.

In an embodiment of the testing apparatus according to the invention, each contact member is configured to be displaced between a first position in which the contact member contacts at least one input terminal of the vaporizer in the associated holding unit, and a second position in which the contact member does not contact an input terminal of the vaporizer in the associated holding unit.

It may be desired, e.g. to provide sufficient space for placing a vaporizer into a holding unit, to use contact members that are displaceable between different positions.

In one of the positions, an unimpeded path for placing a vaporizer into a holding unit is provided, but no contact between the contact member and at least one of the input terminals of the heating element is established, whereas in the other one of the positions, intended to be taken when the vaporizer is held in the holding unit, said path would be impeded, but a contact between the contact member and at least one of the input terminals of the heating element is established.

In an embodiment of the testing apparatus according to the invention, the contact member, which is associated with a holding unit, is in its first position when an outlet opening of a first channel associated with said holding unit is in fluid communication with the inlet port of the fluid duct.

In the first position, in which the contact member contacts at least one input terminal of the vaporizer in the associated holding unit, the heating element of the vaporizer held in the holding unit can be electrically powered, so that vapour produced by the vaporizer will be drawn into the fluid duct when an outlet opening of a first channel associated with said holding unit is in fluid communication with the inlet port of the fluid duct.

In an embodiment of the testing apparatus according to the invention, each contact member comprises a cam track follower, and upon movement of the contact construction part the contact members are positioned in and between the first position and the second position by a cam track engaging the cam track followers of the contact members, wherein the cam track followers are moved relative to the cam track, while moving along the cam track.

The cam track provides a simple and reliable structure to command a time and extent of movement of the contact members between the first and second positions thereof.

In an embodiment of the testing apparatus according to the invention, the cam track is stationary, i.e. stationary relative to the movable contact construction part. A stationary cam track may have a simple structure requiring little maintenance and replacement of worn parts.

In an embodiment of the testing apparatus according to the invention, the holding units form a circular configuration, and the holding construction part is movable in rotation whereby the holding units are moved in a rotation direction.

Accordingly, the vaporizers to be tested can be supplied to holding units of the holding construction part along the holding unit trajectory at a receiving location thereof, and subsequently are transported in a rotation direction along at least part of the holding unit trajectory to perform the testing. A rotating holding construction part can be structured relatively simple, and requires a simple drive, such as a rotating electrical motor, to be driven in rotation.

In further embodiments of the testing apparatus according to the invention, the channel construction part and/or the contact construction part are/is fixed to the holding construction part to be moved in rotation therewith.

In an embodiment of the testing apparatus according to the invention, the slip contacts are fixed to the holding construction part or the contact construction part to be moved in rotation therewith.

In a second aspect of the invention, a method of testing vapour generation capability of vaporizers for electronic cigarettes, or electronic cigarettes or parts thereof comprising vaporizers, is provided, each vaporizer comprising a liquid holder forming a chamber with a filler material retaining a liquid to be vaporized, a heating element, input terminals connected to the heating element for electrically powering the heating element, and a vapour output, whereby the vaporizer is to generate vapour emerging from the vapour output when a current flows through the input terminals in the heating element. The method comprises: electrically powering the input terminals of the heating element of the vaporizer; generating a flow of fluid from the vapour output through a fluid duct while the input terminals of the heating element of the vaporizer are powered; and sensing an amount of vapour present in the fluid duct.

As explained above, the step of electrically powering the input terminals of the heating element can be performed by bringing the input terminals of the heating element into contact with a power supply through electrical contact members or, if operable electronic cigarettes are tested, by drawing air into the electronic cigarette to activate it, whereby the battery of the electronic cigarette electrically powers the input terminals of the heating element.

In an embodiment of the method of the present invention, the sensed amount of vapour is compared with a predetermined lower and/or higher threshold and, if the sensed amount of vapour is below the predetermined lower threshold or above the predetermined higher threshold, then the vaporizer is rejected, otherwise it is approved.

In an embodiment of the method of the present invention, the powering, generating, and sensing steps are repeated; and after each sensing step, a flow of air is generated through the duct.

These and other aspects of the invention will be more readily appreciated as the same becomes better understood by reference to the following detailed description and considered in connection with the accompanying drawings in which like reference symbols designate like parts.

DETAILED DESCRIPTION OF EMBODIMENTS

In the following, embodiments of (parts of) a testing apparatus according to the invention are described. The testing apparatus is constructed and arranged for testing vaporizers of electronic cigarettes. Also, an electronic cigarette or part thereof comprising the vaporizer can be tested in an embodiment of the testing apparatus according to the invention. Initially, embodiments of the testing apparatus for testing a vaporizer as such, or a part of an electronic cigarette including a vaporizer but excluding an electrical power source (e.g. a battery), will be described.

As is well known by the person skilled in the art, each vaporizer comprises a liquid holder forming a chamber with a filler material retaining a liquid to be vaporized, a heating element, input terminals connected to the heating element for electrically powering the heating element, and a vapour output, whereby the vaporizer is to generate vapour emerging from the vapour output when a current flows through the input terminals in the heating element. Air can flow through the vaporizer, such as through the chamber with the filler material, so that vapour generated in the vaporizer will be mixed with air at the vapour output. The vaporizers, when depicted in one of the Figures, are shown as a cylindrically shaped object, although in practice they may have slightly different shapes.

FIGS. 1, 2, 3 and 4 show various aspect of a testing apparatus 1. The testing apparatus 1 may have a frame plate 2 for mounting different parts. A supply unit 4 has vaporizers 6 placed in holding units 8, and places the vaporizers 6 in holding units 10 of a holding construction part 12 at a receiving location along a holding unit trajectory of the holding construction part 12 so that the vaporizers 6 are transported along at least part of the holding unit trajectory. A discharge unit 14 removes the vaporizers 6 from the holding units 10 at a discharge location located on the holding unit trajectory of the holding construction part 12, and takes the vaporizers in holding units 16. A transport unit 18 removes the vaporizers 6 from the holding units 16 of the discharge unit 14 into holding units 20 of the transport unit 18 for further transport.

The supply unit 4, the holding construction part 12, the discharge unit 14, and the transport unit 18 each comprise a rotary wheel 5, 13, 15, 19, respectively having a peripheral surface provided with recesses forming the holding units 8, 10, 16 and 20, respectively. The holding units 8, 10, 16 and 20 clampingly engage the vaporizers 6. Holding units 8, 10, 16 and 20 together with guides 21, 23, 25, respectively, detain the vaporizers 6 along a path of conveyance. The rotary wheels 5, 13, 15, 19 of supply unit 4, holding construction part 12, discharge unit 14, and transport unit 18 comprise a central axis 22, 24, 26, 28 around which they are configured to rotate in a direction of arrows 30, 32, 34, 36, respectively. One or more of the rotary wheels 5, 13, 15, 19 may be driven by a drive (not shown) and/or be mechanically coupled (not shown) by gear wheels to one or more of the other wheels for rotating in synchronism.

Figure 1:
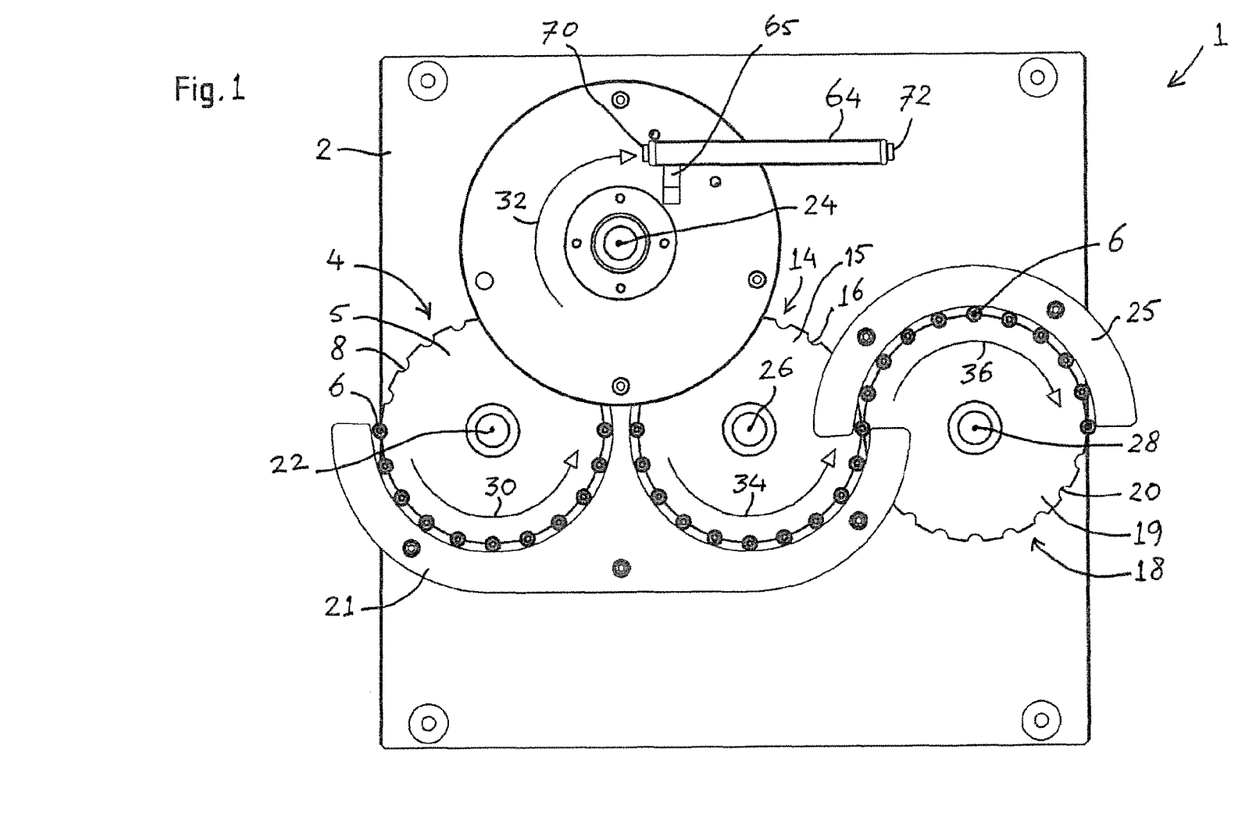
FIG. 1 schematically depicts a top view of an embodiment of a testing apparatus according to the invention, including a supply unit and a discharge unit.
Figure 2:
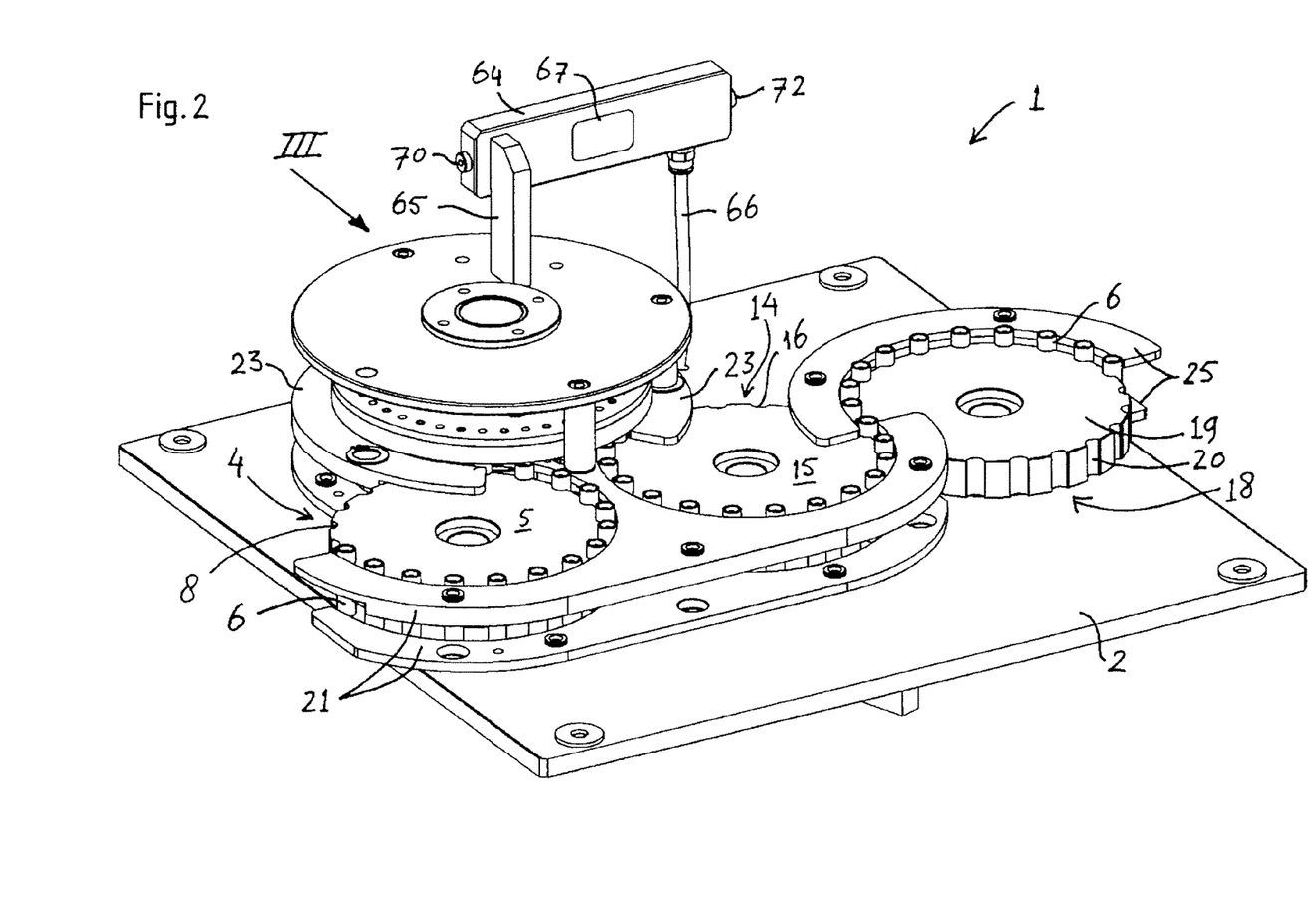
FIG. 2 schematically depicts a perspective view of the embodiment of the testing apparatus of FIG. 1.
Figure 3:
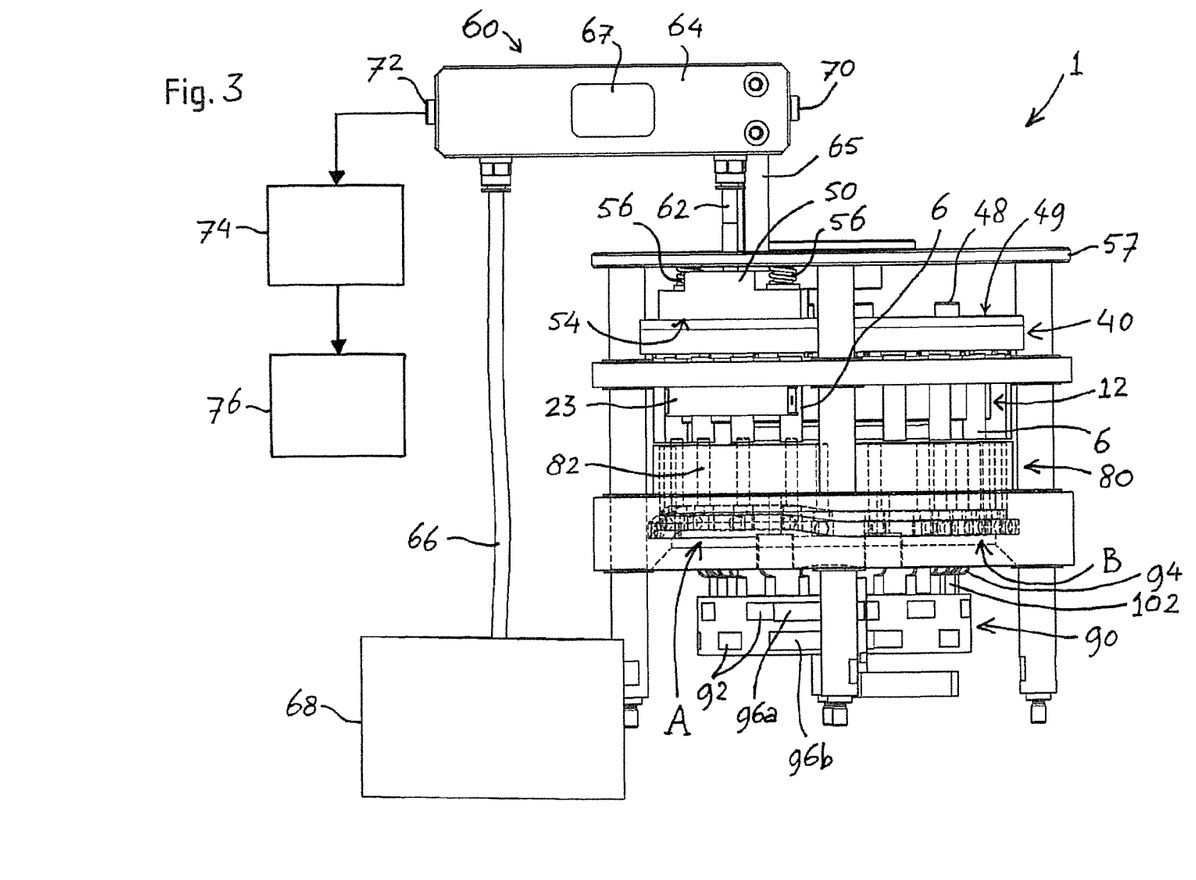
FIG. 3 schematically depicts a side view, taken in a direction III as indicated in FIG. 2, of an embodiment of a testing apparatus according to the invention, partially in diagram.
Figure 4:
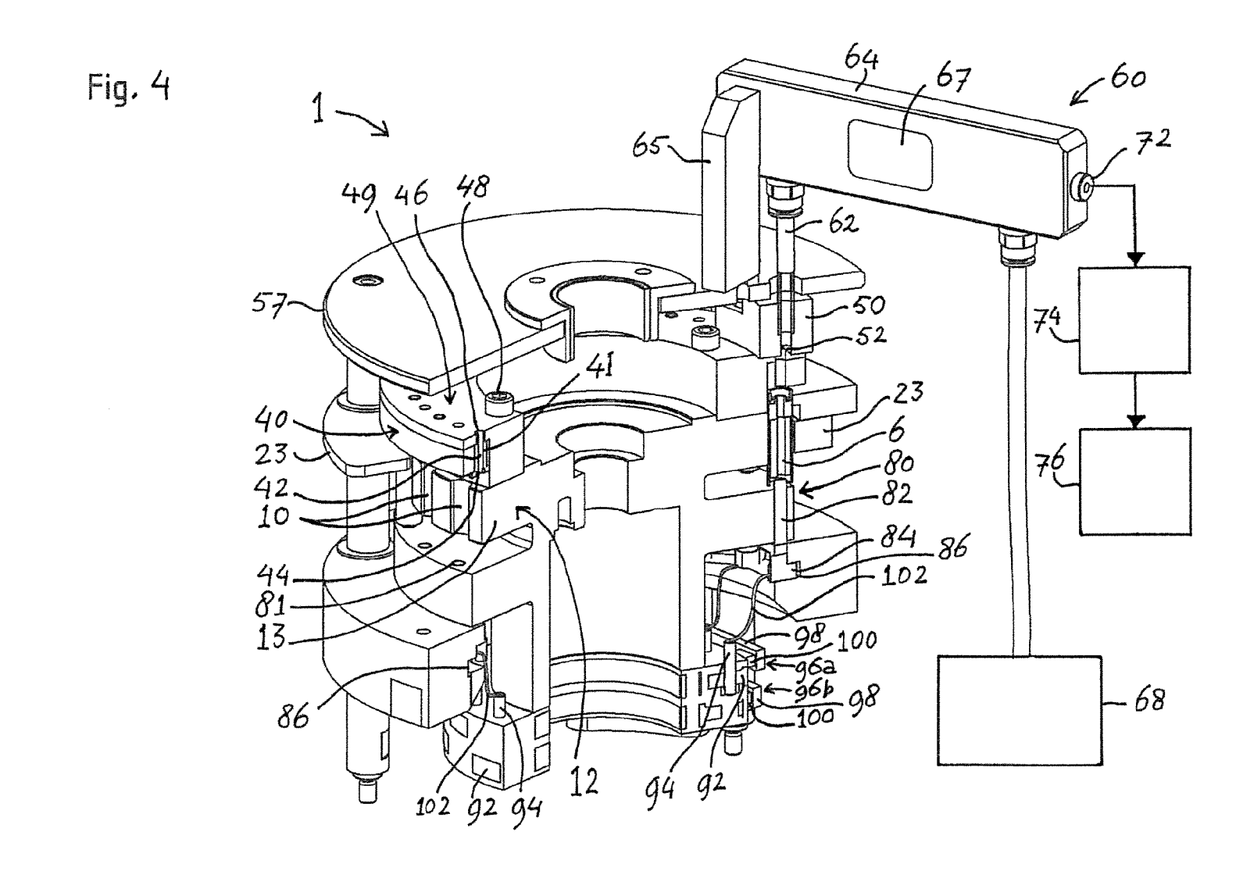
FIG. 4 schematically depicts a perspective view, partially cut away, of the embodiment of the testing apparatus of FIG. 3, again partly in diagram, with no vaporizers accommodated in holding units of a holding construction part at the left-hand part of FIG. 4, and a vaporizer accommodated in a holding unit of the holding construction part at the right-hand part of FIG. 4.
Figure 5:
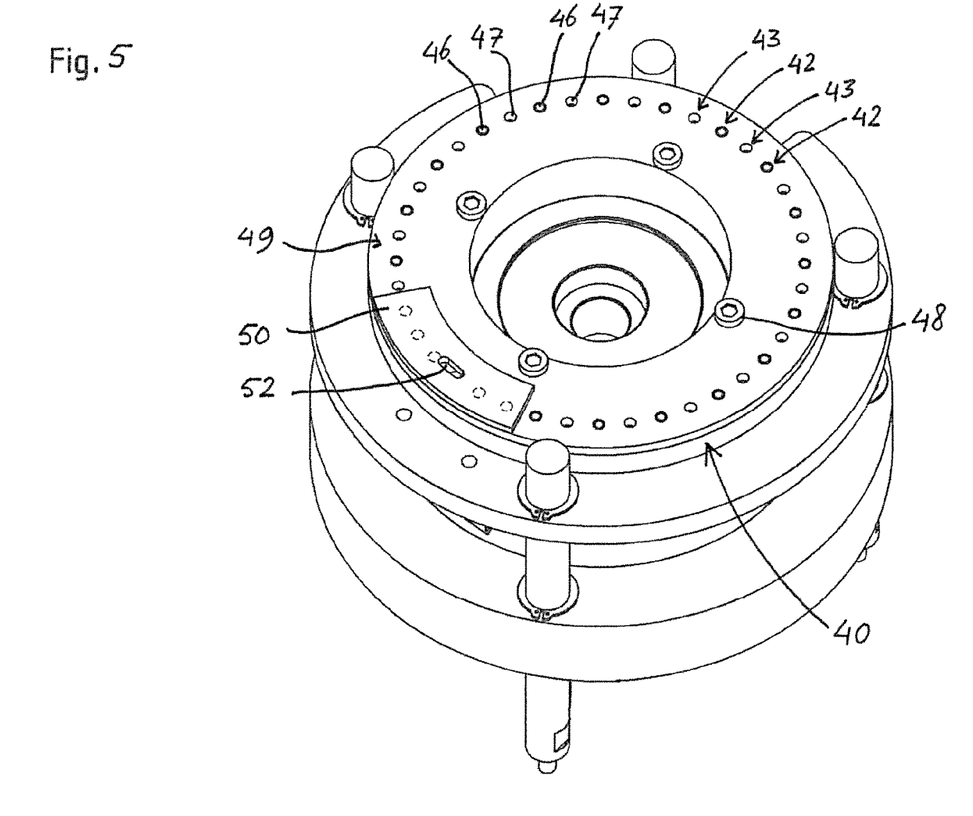
FIG. 5 schematically depicts a perspective view of a portion of an embodiment of a testing apparatus according to the present invention, showing a channel construction part and a cross-sectional view according to plane V-V as indicated in FIG. 6 of a fluid duct inlet part, illustrating an inlet port.

As shown more clearly in FIGS. 3, 4 and 5, an essentially ring-shaped channel construction part 40 is provided with multiple first channels 42 each having an inlet opening 44 and an outlet opening 46, the inlet opening 44 being at one (in the embodiment shown: a lower) side of the channel construction part 40, and the outlet opening 46 being at an opposite (in the embodiment shown: an upper) side of the channel construction part 40. Each first channel is associated with a respective holding unit 10 of the holding construction part 12. The channel construction part 40 is fixed to the holding construction part 12, e.g. by bolts 48 to be moved in rotation therewith. Thus, the channel construction part 40 moves in synchronism with the holding construction part 12, whereby the outlet openings 46 of the first channels 42 move along a circular outlet opening trajectory.

Each first channel 42 comprises an insert 41 whereby the inlet opening 44 of each first channel 42 is provided with a resilient sealing element formed by a lower collar of the insert 41. The inlet opening 44 of each first channel 42 is located to be adjacent to a vapour output of a vaporizer 6 in the associated holding unit 10. The resilient sealing element of the insert 41 faces the vapour output of the vaporizer 6, and is configured to contact the vapour output of a vaporizer 6 in the associated holding unit 10 so that the resilient sealing element may deform to ensure that no environmental gas, such as air, can be drawn into the inlet opening 44 of the first channel 42 along with vapour from the vaporizer 6.

The channel construction part 40 further comprises a plurality of second channels 43 each having an inlet opening and an outlet opening 47. The inlet opening is at one (in the embodiment shown: a lower) side of the channel construction part 40, and the outlet opening 47 is at an opposite (in the embodiment shown: an upper) side of the channel construction part 40. The inlet openings of the second channels 43 are always open to the environment. Each second channel 43 is located in the channel construction part 40 between two consecutive first channels 42. Each outlet opening 47 of a second channel 43 is located in the channel construction part 40 between two consecutive outlet openings 46 of the first channels 42 to be on the outlet opening trajectory. Likewise, each outlet opening 46 of a first channel 42 is located in the channel construction part 40 between two consecutive outlet openings 47 of the second channels 43.

Figure 6:
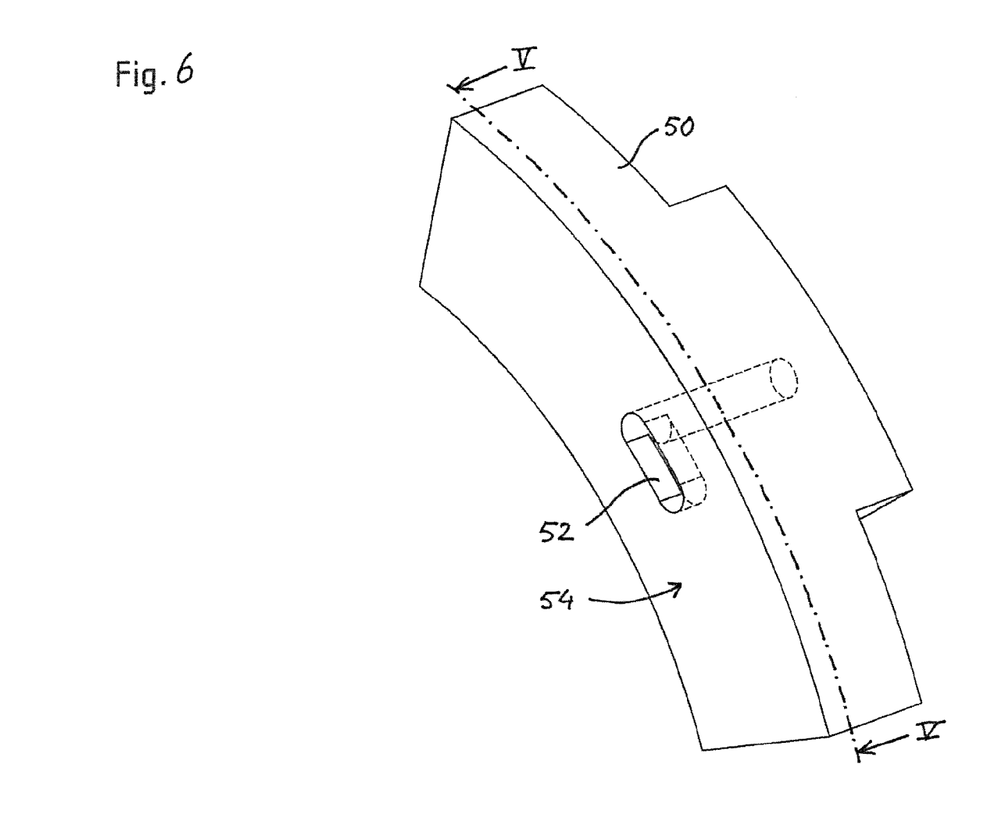
FIG. 6 schematically depicts a perspective view of an inlet port of a fluid duct of an embodiment of a testing apparatus, such as the embodiment of FIG. 3 or 4, according to the present invention.

A fluid duct inlet part 50 having an inlet port 52 (FIGS. 5, 6) on a surface 54 is mounted stationary adjacent to the outlet openings 46 of the first channels 42 and the outlet openings 47 of the second channels 43 such that the inlet port 52 is located to be adjacent to the outlet opening trajectory. As shown in FIGS. 3, 5 and 6, the surface 54 of the fluid duct inlet part 50 adjoins a surface 49 on which the outlet openings 46 of the first channels 42 and the outlet openings 47 of the second channels 43 are located. The fluid duct inlet part 50 is biased by springs 56 relative to a stationary frame part 57 to press the surfaces 49 and 54 towards each other.

The inlet port 52 of the fluid duct inlet part 50 extends along a portion of the outlet opening trajectory. This portion of the outlet opening trajectory is selected such that, upon movement (here: rotation) of the channel construction part 40, and thereby movement of the outlet openings 46, 47 in rotation along the outlet opening trajectory in a direction of arrow 32 relative to the inlet port 52, the inlet port 52 consecutively is in fluid communication with a first channel 42, a combination of a first channel 42 and a second channel 43, a second channel 43, a combination of a second channel 43 and a first channel 42, a first channel 42, etc. Thus, the inlet port 52 never is closed off by the surface 49, and always is in fluid communication with one of, or both of, a first channel 42 and a second channel 43.

As shown in FIGS. 3, 4 and 6, the fluid duct inlet part 50 forms part of a fluid duct 60 further comprising a pipe 62, a chamber 64 mounted on a support 65 that in turn is mounted on the stationary frame part 57, and a pipe 66. The fluid duct 60 is connected to a fluid pump 68 (only diagrammatically shown) to create a fluid flow in the fluid duct 60 in a direction from the inlet port 52 through the fluid duct inlet part 50, the pipe 62, the chamber 64 and the pipe 66. Since upon rotation of the channel construction part 40 the inlet port 52 consecutively is in fluid communication with a first channel 42, a combination of a first channel 42 and a second channel 43, or a second channel 43, the fluid flow may be continuous.

The chamber 64 has non-transparent walls except for a transparent window 67 providing a view of the inside of the chamber 64.

A light source 70 is mounted at an end of the chamber 64 to radiate light inside the chamber 64 directed to a light detector or sensor mounted at an opposite end of the chamber 64. The light sensor constitutes a vapour sensor 72 arranged in the fluid duct 60, since the amount of light received by the light-detecting vapour sensor 72 from the light source 70 depends from the amount of vapour in the chamber 64. The higher the amount of vapour in the chamber 64, the lower the amount of light received by the vapour sensor 72, and the lower the amount of vapour in the chamber 64, the higher the amount of light received by the vapour sensor 72.

As illustrated in FIGS. 3 and 4, the vapour sensor 72 is configured to provide a sensing signal indicating an amount of vapour present in the (chamber 64 of the) fluid duct 60. The sensing signal is supplied to a control device 74. The control device 74 is configured to acquire the sensing signal after the inlet port 52 of the fluid duct 60 has come in fluid communication with a first channel 42. The control device 74 further is configured to compare the sensed amount of vapour with a predetermined lower and/or higher threshold, and to actuate an ejection device 76 if the sensing signal indicates the amount of vapour to be below the predetermined lower threshold and/or above the predetermined higher threshold.

Referring to FIGS. 3 and 4, the testing apparatus 1 further comprises an essentially ring-shaped contact construction part 80 provided with multiple electrical contact members 82, wherein each contact member 82 is associated with a respective holding unit 10 of the holding construction part 12, and is configured to contact at least one input terminal of a vaporizer 6 in the associated holding unit 10. In the embodiment shown, the contact construction part 80 is fixed to the holding construction part 12 to be moved in rotation in synchronism therewith.

Each contact member 82 is configured to be displaced between a first position in which the contact member contacts at least one input terminal of a vaporizer 6 in the associated holding unit 10, and a second position in which the contact member 82 does not contact an input terminal of the vaporizer 6 in the associated holding unit 10. In particular, each contact member 82 comprises a cam track follower 84, and upon movement of the contact construction part 80 the contact members 82 are positioned in and between the first position and the second position thereof by a stationary cam track 86 engaging the cam track followers 84 of the contact members 82, wherein the cam track followers 84 move relative to the cam track 86, and the contact members 82 slide in channels 81 provided in the contact construction part 80.

As is shown in particular in FIG. 3, the cam track 86 comprises a sectional part A bringing the contact members 82 by displacement of their cam track followers 84 to the first position thereof to contact at least one input terminal of the vaporizers 6 held in the associated holding units 10. In a sectional part B of the cam track 86, the contact members 82 by displacement of their cam track followers 84, are brought to the second position thereof to have no contact with an input terminal of the vaporizers 6 held in the associated holding units 10.

As further shown in FIGS. 3 and 4, each contact member 82 is in its first position when an outlet opening 46 of a first channel 42 associated with a holding unit 10 associated with the contact member 82 is in fluid communication with the inlet port 52 of the fluid duct 60.

Figure 7:
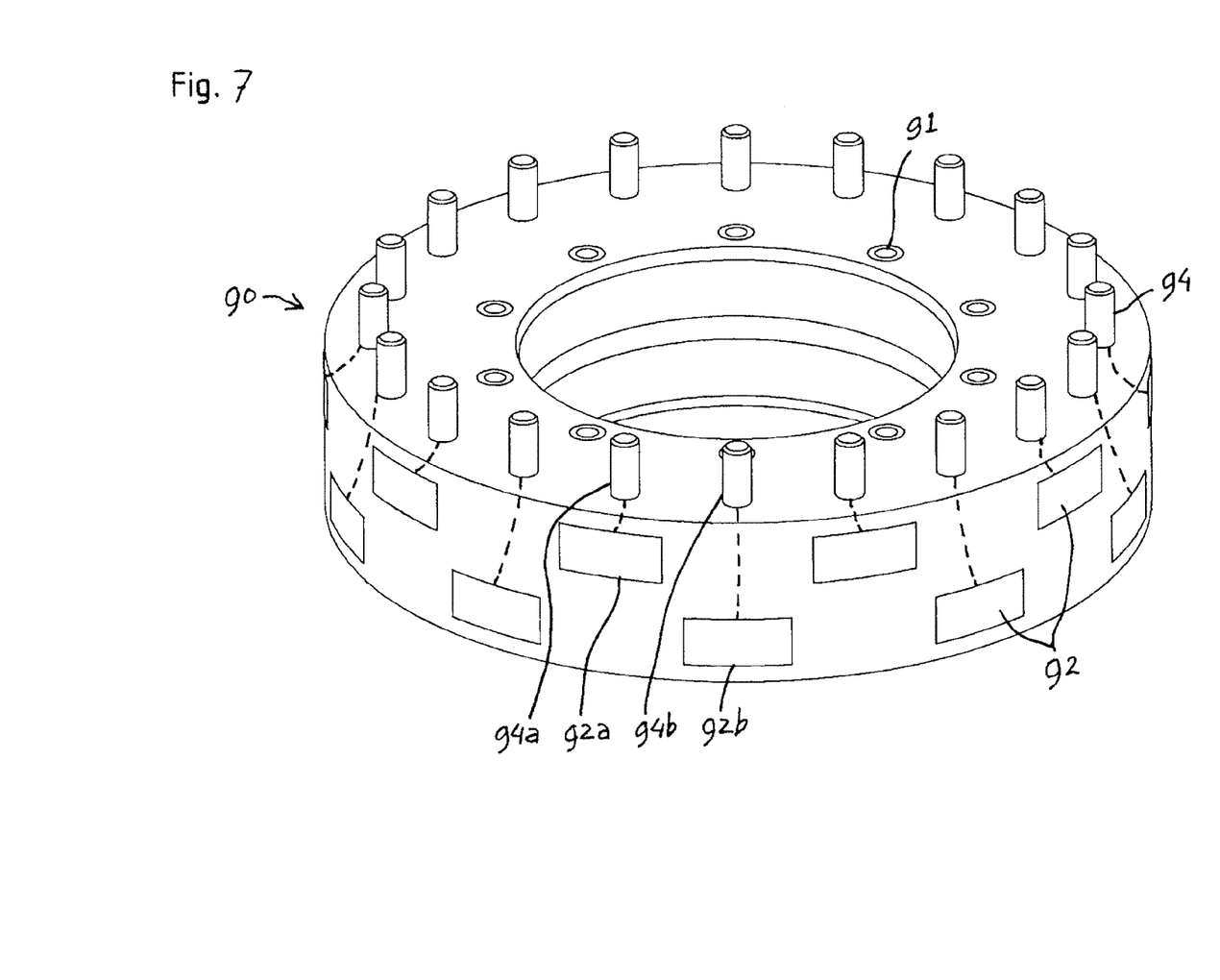
FIG. 7 schematically depicts a perspective view of a supply construction part of the testing apparatus of FIG. 3 or 4.

Referring to FIGS. 3, 4 and 7, the testing apparatus 1 further comprises an essentially ring-shaped supply construction part 90. The supply construction part 90 is adapted to be moved, in particular to be rotated, in synchronism with the contact construction part 80. For this purpose, the supply construction part 90 is fixed to the contact construction part 80 by bolts (not shown) passing through holes 91.

The supply construction part 90 is provided with multiple electrical slip contacts 92 mounted in an electrically isolating body. Each slip contact 92 is electrically connected to an associated electrically conducting pin 94 mounted in the electrically isolating body of the supply construction part 90, and such connection is symbolically indicated by dashed lines in FIG. 7. For illustration, slip contact 92a is electrically connected to pin 94a, and slip contact 92b is electrically connected to pin 94b. Every other one of the slip contacts 92, as seen along the circumference of the supply construction part 90, is located in a lower or higher part of the supply construction part 90.

Two stationary power supply terminals 96a, 96b are arranged and configured to electrically contact and power slip contacts 92. The power supply terminals 96a, 96b each comprise an electrically conducting arm 98 and an electrically conducting pad 100. The arms 98 are biased towards the supply construction part 90. Upon rotation of the supply construction part 90, the pad 100 of power supply terminal 96a is to contact different slip contacts 92 in a higher part of the supply construction part 90, while the pad 100 of power supply terminal 96b is to contact different slip contacts 92 in a lower part of the supply construction part 90. In operation, the power supply terminals 96a, 96b are supplied with a voltage.

Each slip contact 92 is electrically connected to an associated contact member 82 through an associated pin 94 and a flexible wire 102.

The location of the power supply terminals 96a, 96b, in particular of the pads 100 thereof, is selected such that the power supply terminals 96a, 96b electrically contact and power a slip contact 92 associated with a contact member 82, which in turn is associated with a holding unit 10, when an outlet opening 46 of a first channel 42 associated with said holding unit 10 is in fluid communication with the inlet port 52 of the fluid duct 60.

Next, the operation of the testing apparatus 1 will be described and explained in further detail.

In operation, vaporizers 6 are supplied to holding units 10 by the supply unit 4 at a receiving location along a holding unit trajectory of the holding construction part 12 so that the vaporizers 6 are transported along at least part of the holding unit trajectory. Considering the direction of rotation 32 of the holding construction part 12, the receiving location is associated with a sectional part B of the cam track 86, upstream of the sectional part A of cam track 86.

For each vaporizer 6 to be tested and held in a holding unit 10, when the cam track follower 84 of the associated contact member 82 is in the sectional part B outside the sectional part A of cam track 86, the vaporizer 6 is not electrically powered to produce vapour, and no fluid flow is generated in the first channel 42 associated with the holding unit 10. Each first channel 42 associated with a holding unit 10 holding a vaporizer 6 has its inlet opening 44 in fluid communication with the vapour outlet of the vaporizer 6, and has its outlet opening 46 in fluid communication with the atmosphere surrounding the testing apparatus 1.

For each vaporizer 6 held in a holding unit 10, when the cam track follower 84 of the associated contact member 82 enters the sectional part A of cam track 86, the contact member 82 is displaced towards the vaporizer 6 by the cam track follower 84 being displaced in the cam track 86. By such displacement, the contact member 82 contacts an input terminal of the heating element of the vaporizer 6. Here, it is assumed that another input terminal of the heating element of the vaporizer 6 is formed by an external wall or part thereof of the vaporizer 6, the other input terminal contacting a part of the holding unit 10 electrically connected to mass. At this point in the testing process, the contact member 82 is not electrically powered.

Next, for each vaporizer 6 held in a holding unit 10, when the outlet opening 46 of the associated first channel 42 is in fluid communication with the inlet port 52 of the fluid duct 60, or even before this situation commences, the slip contact 92 that is connected to the contact member 82 through pin 94 and wire 102, is powered by one of the power supply terminals 96a, 96b, at most during a time that the pad of the power supply terminal 96a, 96b contacts the slip contact 92, or during a shorter period of time. As a result, the contact member 82 electrically powers the input terminal of the heating element of the vaporizer 6.

If the vaporizer 6 is fully functional, the electrically powering of the input terminal of the heating element of the vaporizer 6 causes an electrical current to flow in the heating element of the vaporizer 6, which causes the vaporizer 6 to produce vapour. This vapour is drawn into the fluid duct 60 during the time that the first channel 42 is in fluid communication with the inlet port 52 of the fluid duct 60, by the fluid pump 68 creating a low pressure in the fluid duct 60.

If the vaporizer 6 is malfunctioning, e.g. because of a broken heating element, or a connection between an input terminal and the heating element being broken, or lack of liquid to be vaporized, then the electrically powering of the input terminal does not cause the vaporizer 6 to produce vapour, or causes only a low amount of vapour to be produced, or even causes an abnormally high amount of vapour to be produced, and no vapour or a low amount of vapour or an abnormally high amount of vapour is drawn into the fluid duct 60 during the time that the first channel 42 is in fluid communication with the inlet port 52 of the fluid duct 60.

Accordingly, a presence of different amounts of vapour in the fluid duct 60 indicates a fully functional vaporizer 6, or a malfunctioning vaporizer 6, as a result of the testing of the electronic cigarettes in the testing apparatus.

The amount of vapour in the fluid duct 60 is sensed by sensing an amount of light emitted by the light source 70 and impinging on the vapour sensor (light detector) 72. In control device 74, the sensed amount of vapour is compared with a predetermined lower and/or higher threshold and, if the sensed amount of vapour is below the predetermined lower threshold (the sensed amount of light is relatively high, caused by the vaporizer 6 producing no, or an insufficient amount of vapour) or above the predetermined higher threshold (the sensed amount of light is relatively low, caused by the vaporizer 6 producing too much vapour), then rejecting the vaporizer 6, otherwise approving it. In case of rejection, the control device 74 actuates a rejection device 76 at an appropriate location (e.g. included in transport unit 18) and time to remove the vaporizer 6 having a defect from an electronic cigarette production process. The control device 74 may be part of, or integrated with, the vapour sensor 72, or be separate therefrom.

The sensing of the amount of vapour is timed with the electrical powering of each vaporizer 6 and with the overlapping of the outlet opening 46 of the associated first channel 42 and the inlet port 52 of the fluid duct 60, to be able to correlate a particular sensing signal or sensed amount of vapour from the vapour sensor 72 with a particular vaporizer 6.

After testing a vaporizer 6 present on the holding unit trajectory of the testing apparatus 1 as described above, a second channel 43 has its outlet opening 47 overlapping with the inlet port 52 of the fluid duct 60. During that time, an environmental gas, e.g. air surrounding the testing apparatus 1, will be drawn into the fluid duct 60 through the second channel 43 to remove vapour in the fluid duct 60 before the next vaporizer 6 present on the holding unit trajectory is tested.

After testing a vaporizer 6, the cam track follower 84 of the associated contact member 82 moves from sectional part A of cam track 86 to sectional part B of cam track 86, whereby the contact member 82 is displaced away from the vaporizer 6 by its cam track follower 84 being displaced in the cam track 86. The tested vaporizer 6 is removed from the holding unit 10 at the discharge location of the holding unit trajectory.

In another embodiment of the testing apparatus, wherein functional electronic cigarettes are tested, instead of vaporizers as such or electronic cigarette parts including a vaporizer but excluding an electrical power source, a contact construction part 80 and a supply construction part 90 may essentially be omitted. In such embodiment of the testing apparatus, each holding unit 10 is configured to hold an electronic cigarette with its vapour output adjacent the inlet opening 44 of an associated first channel 42. When the outlet opening 46 of the first channel 42 is in fluid communication with the inlet port 52 of the fluid duct 60, air is drawn through the electronic cigarette whereby it should be activated. In a variant in which the supply construction part 90 is omitted, but the contact construction part is present, the contact members of the contact construction part need not have an electrical function since this is incorporated in the tested operable electronic cigarette, but serve to provide a mechanical function to bring the electronic cigarettes into a position wherein the vapour output is in optimum fluid communication with the first channel of the channel construction part.

If the electronic cigarette is fully functional, the activation thereof leads to electrically powering of the input terminals of the heating element of the vaporizer, whereby an electrical current flows in the heating element of the vaporizer, which causes the vaporizer to produce vapour. This vapour is drawn into the fluid duct 60 during the time that the first channel 42 is in fluid communication with the inlet port 52 of the fluid duct 60, by the fluid pump 68 creating a low pressure in the fluid duct 60.

If the electronic cigarette is malfunctioning, e.g. because of a defect air flow sensor, or a broken heating element, or a connection between an input terminal and the heating element being broken, or lack of liquid to be vaporized, then there is no activation of the electronic cigarette, or there is an activation but the electrically powering of the input terminals of the heating element of the vaporizer does not cause the vaporizer to produce vapour, or causes only a low amount of vapour to be produced, or even causes an abnormally high amount of vapour to be produced, and no vapour or a low amount of vapour or an abnormally high amount of vapour is drawn into the fluid duct 60 during the time that the first channel 42 is in fluid communication with the inlet port 52 of the fluid duct 60.

Accordingly, a presence of different amounts of vapour in the fluid duct 60 indicates a fully functional electronic cigarette, or a malfunctioning electronic cigarette, as a result of the testing of the electronic cigarettes in the testing apparatus.

As explained above, a testing apparatus for testing vaporizers of electronic cigarettes comprises a movable holding construction part provided with multiple holding units each for holding a vaporizer. A channel construction part adapted to be moved synchronously with the holding construction part is provided with multiple first channels each having an inlet opening and an outlet opening, wherein each first channel is associated with a respective holding unit. The inlet opening of each first channel is located to be adjacent to the vapour output of a vaporizer in the associated holding unit. The outlet openings of the first channels move along an outlet opening trajectory. A fluid duct has a stationary inlet port adjacent to the outlet opening trajectory. The fluid duct is connected to a fluid pump to create a fluid flow in the fluid duct in a direction away from the inlet port. A vapour sensor is arranged in the fluid duct.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in an appropriately detailed structure. Further, the terms and phrases used hereinabove are not intended to be limiting, but rather, to provide an understandable description of the invention.

The terms "a"/"an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The term coupled, as used herein, is defined as connected, although not necessarily directly, and not necessarily mechanically.

A single processor or other unit may fulfil the functions of several items recited in the claims.

The invention claimed is:

1. A testing apparatus for testing vaporizers of electronic cigarettes, or electronic cigarettes or parts thereof comprising the vaporizers, each vaporizer comprising a liquid holder forming a chamber retaining a liquid to be vaporized, a heating element, input terminals connected to the heating element for electrically powering the heating element, and a vapour output, whereby the vaporizer is to generate vapour emerging from the vapour output when a current flows through the input terminals in the heating element, the testing apparatus comprising:

a holding construction part provided with multiple holding units each for holding a vaporizer, or an electronic cigarette or part thereof comprising the vaporizer, wherein the holding units are positioned at a holding distance from each other, and wherein the holding construction part is movable whereby the holding units are moved along a holding unit trajectory;

a channel construction part provided with multiple first channels each having an inlet opening and an outlet opening, wherein each first channel is associated with a respective holding unit, wherein the inlet opening of each first channel is located to be in fluid communication with the vapour output of a vaporizer in the associated holding unit, and wherein the channel construction part is adapted to be moved in synchronism with the holding construction part whereby the outlet openings of the first channels move along an outlet opening trajectory;

a fluid duct having an inlet port located to be adjacent to the outlet opening trajectory, wherein the fluid duct is connected to a fluid pump to create a fluid flow in the fluid duct in a direction away from the inlet port, and wherein the channel construction part moves relative to the inlet port of the fluid duct; and a vapour sensor arranged in the fluid duct.

2. The testing apparatus according to claim 1, wherein the inlet port of the fluid duct is stationary.

3. The testing apparatus according to claim 1, wherein the channel construction part further comprises a plurality of second channels each having an inlet opening and an outlet opening, wherein the inlet openings of the second channels are open to the environment, and wherein each outlet opening of a second channel is located in the channel construction part between two consecutive outlet openings of the first channels to be on the outlet opening trajectory.

4. The testing apparatus according to claim 3, wherein the inlet port of the fluid duct extends along a portion of said outlet opening trajectory to be in fluid communication with a first channel, a combination of a first channel and a second channel, or a second channel, upon movement of the channel construction part.

5. The testing apparatus according to claim 1, wherein the inlet opening of each first channel is provided with a resilient sealing element configured to contact the vapour output of a vaporizer in the associated holding unit.

6. The testing apparatus according to claim 1, wherein the vapour sensor is configured to provide a sensing signal indicating an amount of vapour present in the fluid duct, and wherein the testing apparatus further comprises a control device configured to:

acquire the sensing signal after the inlet port of the fluid duct has come in fluid communication with a first channel;

comparing the sensed amount of vapour with a predetermined lower and/or higher threshold; and provide a control signal indicating a rejection of the vaporizer when the sensed amount of vapour is below the predetermined lower threshold or above the predetermined higher threshold, or indicating an approval of the vaporizer otherwise.

7. The testing apparatus according to claim 6, wherein the control device further is configured to:

actuate an ejection device if the sensing signal indicates the amount of vapour to be below the predetermined lower threshold or above the predetermined higher threshold.

8. The testing apparatus according to claim 6, wherein the vapour sensor comprises a light detector, wherein the light detector is adapted to sense a transmission or reflection of light from a light source to a path of vapour in the fluid duct.

9. The testing apparatus according to claim 1, further comprising:

a contact construction part provided with multiple contact members, wherein each contact member is associated with a respective holding unit, and is configured to contact the vaporizer in the associated holding unit, and wherein the contact construction part is adapted to be moved in synchronism with the holding construction part.

10. The testing apparatus according to claim 9, wherein the contact members are electrical contact members, and wherein the electrical contact members are configured to contact at least one input terminal of the vaporizer in the associated holding unit, the testing apparatus further comprising:

a supply construction part provided with:

multiple electrical slip contacts, wherein each slip contact is associated with a respective contact member, wherein the slip contact is electrically connected to an associated contact member, and wherein the supply construction part is adapted to be moved in synchronism with the contact construction part; and at least one stationary power supply terminal configured to electrically contact and power a slip contact associated with a contact member, which in turn is associated with a holding unit, when an outlet opening of a first channel associated with said holding unit is in fluid communication with the inlet port of the fluid duct, wherein the slip contacts are adapted to move relative to the power supply terminal.

11. The testing apparatus according to claim 9, wherein each contact member is configured to be displaced between a first position in which the contact member contacts at least one input terminal of the vaporizer in the associated holding unit, and a second position in which the contact member does not contact an input terminal of the vaporizer in the associated holding unit.

12. The testing apparatus according to claim 11, wherein the contact member, which is associated with a holding unit, is in its first position when an outlet opening of a first channel associated with said holding unit is in fluid communication with the inlet port of the fluid duct.

13. The testing apparatus according to claim 11, wherein each contact member comprises a cam track follower, and wherein upon movement of the contact construction part the contact members are positioned in and between the first position and the second position by a stationary cam track engaging the cam track followers of the contact members, wherein the cam track followers are moved relative to the cam track while moving along the cam track.

14. The testing apparatus according to claim 1, wherein the holding units form a circular configuration, wherein the holding construction part is movable in rotation whereby the holding units are moved in a rotation direction, and wherein the channel construction part is fixed to the holding construction part to be moved in rotation therewith.

15. The testing apparatus according to claim 14, wherein the contact construction part is fixed to the holding construction part to be moved in rotation therewith.

16. The testing apparatus according to claim 14, wherein the slip contacts are fixed to the holding construction part or the contact construction part to be moved in rotation therewith.

17. The testing apparatus according to claim 1, further comprising:
a supply unit which places the vaporizers, or electronic cigarettes or parts thereof comprising the vaporizers, in the holding units of the holding construction part at a receiving location along the holding unit trajectory so that the vaporizers, or electronic cigarettes or parts thereof comprising the vaporizers, are transported along at least part of the holding unit trajectory, and
a discharge unit which removes the vaporizers, or electronic cigarettes or parts thereof comprising the vaporizers, from the holding units at a discharge location along the holding unit trajectory.

18. A method of testing vapour generation capability of vaporizers for electronic cigarettes, or electronic cigarettes or parts thereof comprising the vaporizers, each vaporizer comprising a liquid holder forming a chamber retaining a liquid to be vaporized, a heating element, input terminals connected to the heating element for electrically powering the heating element, and a vapour output, whereby the vaporizer is to generate vapour emerging from the vapour output when a current flows through the input terminals in the heating element, the method comprising:
holding a plurality of vaporizers in respective holding units;
providing one fluid duct having an inlet port; and
for each vaporizer of the plurality of vaporizers:
moving the holding unit to bring the vapour output of the associated vaporizer into fluid communication with the inlet port of the fluid duct;
electrically powering the input terminals of the heating element of the vaporizer;
generating a flow of fluid from the vapour output through the fluid duct in a direction away from the inlet port, while the input terminals of the heating element of the vaporizer are powered; and
sensing an amount of vapour present in the fluid duct.

19. The method of claim 18, further comprising comparing the sensed amount of vapour with a predetermined lower and/or higher threshold and, if the sensed amount of vapour is below the predetermined lower threshold or above the predetermined higher threshold, then rejecting the vaporizer, otherwise approving it.

20. The method of claim 18, further comprising:
after each sensing step, generating a flow of air through the fluid duct.

* * * * *